United States Patent [19]

Carter

[11] Patent Number: 4,989,599
[45] Date of Patent: Feb. 5, 1991

[54] DUAL LUMEN CANNULA

[75] Inventor: William Carter, Indianapolis, Ind.

[73] Assignee: Puritan-Bennett Corporation, Overland Park, Kans.

[21] Appl. No.: 302,188

[22] Filed: Jan. 26, 1989

[51] Int. Cl.$^5$ ............................................. A61M 15/08
[52] U.S. Cl. .......................... 128/207.18; 128/204.18; 128/204.26
[58] Field of Search ........... 128/716, 720, 725, 203.18, 128/203.22, 204.12, 204.18, 204.26, 206.11, 207.18, 204.23

[56] References Cited

U.S. PATENT DOCUMENTS

| 3,172,407 | 3/1965 | Von Pechmann | 128/207.18 |
| 4,054,133 | 10/1977 | Myers | 128/207.18 |
| 4,484,578 | 11/1984 | Durkan | 128/204.26 |

Primary Examiner—David A. Wiecking
Assistant Examiner—Aaron J. Lewis
Attorney, Agent, or Firm—Robert A. Spray

[57] ABSTRACT

Cannula apparatus for respiration therapy, having a pair of body members, each having a pair of cannulae for providing a cannula nipple outlet for each of a person's nostrils, the two body members respectively delivering gas to each of the person's nostrils, and monitoring the respiration of each of the person's nostrils. One of the body members is carried inwardly of the other, its cannulae also carried inwardly of those of the other, achieving the patient comfort of only feeling a single cannula in each nostril, yet the gas and monitoring lumens and their outlets are separate for good operativity of respiration and breathing-monitoring. Interchangeability of the body members and their respective tubing is providing by operative equality of areas of the cylindrical and annular passages.

14 Claims, 2 Drawing Sheets

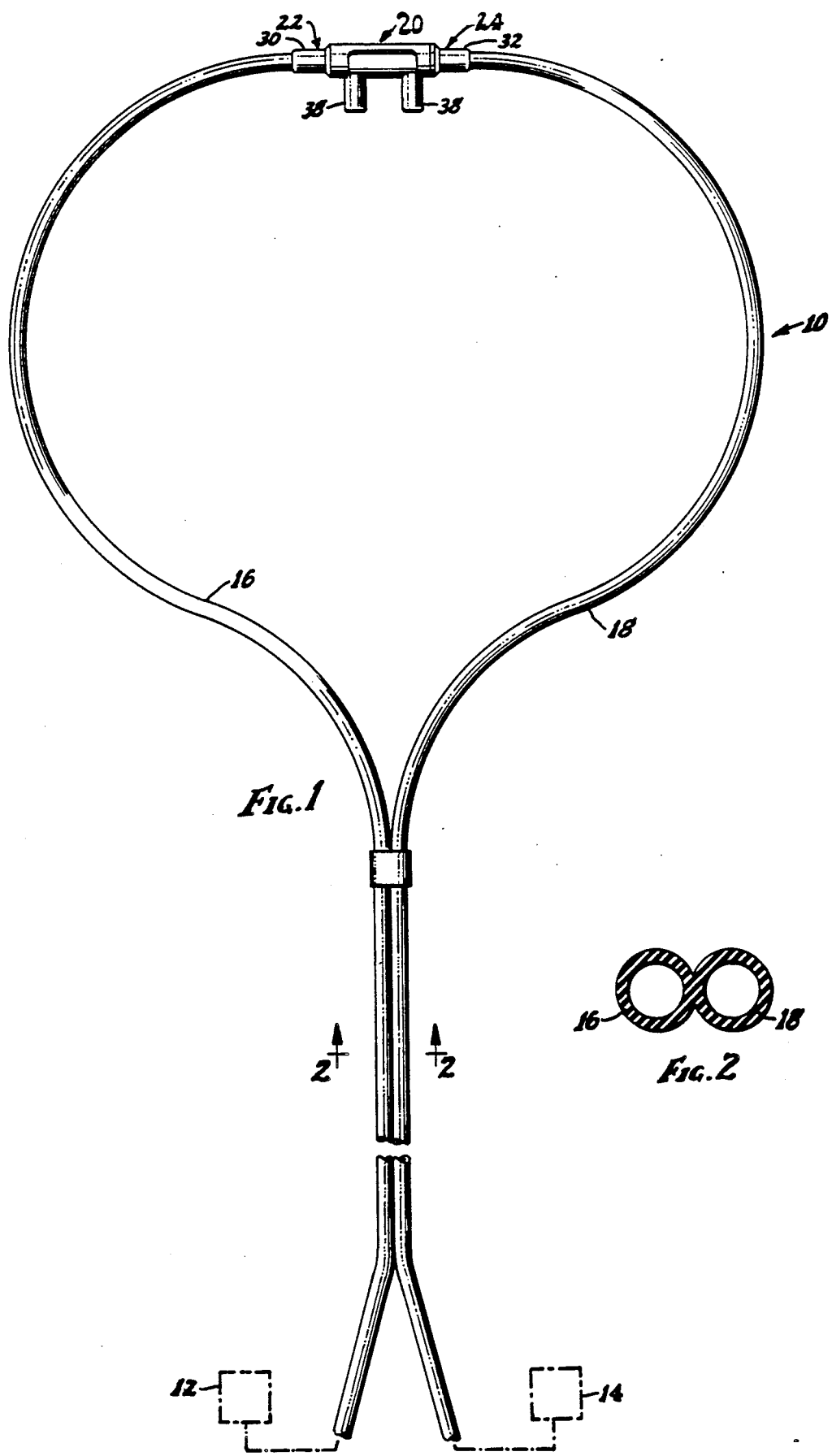

DUAL LUMEN CANNULA

FIELD OF THE INVENTION

This invention relates to respiration therapy, and more particularly to respiration therapy in which a gas (usually oxygen or an oxygen/air mixture) is to be delivered into a patient's nostrils by some sort of a cannula inserted into the patient's nose, and a breathing-monitoring cannula is also needed in close proximity to control details of the overall respiration-therapy equipment and procedure.

Such details, i.e., of breathing-monitoring, control of pressure and supply of the respiration gas, sequential setting of the respiration equipment components, etc., are not part of this invention, but they are mentioned to indicate the reason for the breathing-monitoring function to be needed; and since that breathing-monitoring function is needed, that is the reason why breathing-monitoring cannulae are needed in the patient's nose even though the presence of an extra cannula in each nostril is a source of extra bother and discomfort to the patient, who is likely to find any sort of respiration therapy disagreeable to say the least.

With such respiration therapy, therefore, the presence of two cannulae has long been known to be needed, in a dual arrangement providing a pair of cannulae and their gas-delivery or monitoring bores (lumens) in a sort of harness, with one tube going to the oxygen or air/oxygen supply, and one tube connected to either some monitor/control equipment or to another gas.

Against that background, the present invention's achievements are to provide better patient comfort, ease and convenience for the attendant, good operativity, etc.

SUMMARY OF THE INVENTION

In carrying out the invention, there are provided a pair of body members, one being an inner one and one being an outer one, each having a primary bore and a spaced pair of cannula nipples.

One of the cannula nipples of the outer body member, and one of the cannula nipples of the inner body member, respectively, are provided as a set, for each of a person's nostrils; and each set provides for one of the body members a respiration gas and either a monitoring of that gas or a supply of a different gas.

The cannula nipples of the inner body member are made to be sufficiently flexible, preferably by the inner body member being formed integrally with its cannula nipples, all from a flexible material, that assembly is achieved by pushing the inner body into an open end of the outer body; and this flexibility accommodates assembly even though the nipples of both body members extend transversely of the portion of the body member having its primary bore.

Interchangeability of either the inner body member and outer body member provides for convenience of use; and this interchangeability is achieved by providing all corresponding portions of the inner and outer body members of operatively equal cross-sectional bore areas, i.e., the cross-sectional area of the inner body member is operatively equal to the cross-sectional area of the outer body member minus the cross-sectional area of the outer surface of the inner body member.

The prior art does not show the inventive concepts, even though patient-therapy has long utilized modified respiration using cannulae The prior art therapy has long provided various modifications of human respiration, particularly oxygen and or oxygen/air mixtures; and, since it has been long known that the supply and rate of oxygen delivery to the patient must be kept within prescribed limits, and since supply-control equipment has been provided which senses respiration as a means of economizing the oxygen delivery, the prior art has provided not only an oxygen-supply tube arrangement but also a respiration-monitoring tube to control the oxygen supply.

And since humans have two nostrils, and since the respiration of the two nostrils is often significantly different, the prior art has provided both an oxygen-supply tube and a breath-monitoring tube for each nostril.

Yet not only is oxygen therapy itself bothersome and annoying to many patients, the extra monitoring tube use, making two tubes for each nostril, all accumulate to make oxygen therapy of additional discomfort to the patient, especially of course with the other discomforts of the therapy environment and situation.

The prior art has provided monitoring equipment for monitoring the respiration cycle of a patient (inhaling, dwell, and exhaling periods) so as to cause the oxygen or oxygen/air to be forced to the patient only at certain periods of the cycle (for both patient-comfort and oxygen economy); and that monitoring has been provided by tubing whose open or sensing end is in close proximity to the oxygen or oxygen/air outlet.

It has apparently seemed inevitable to the prior art, or at least an inherent incident of oxygen supply and breath-monitoring, that separate tubes be provided for the oxygen-supply and for the breath-monitoring operativity for each nostril, and that each of the set for each nostril be kept separate to avoid undue masking of the respiration by the oxygen supply.

With this background, the significance of the present invention, by which the patient is required to be bothered by only a single cannula nipple in each nostril, is better seen to be quite advantageous, making the oxygen therapy less bothersome and more endurable.

In a hindsight consideration of the present invention to determine its inventive and novel nature, it is not only conceded but emphasized that the prior art had details usable in this invention but only if the prior art had had the guidance of the present concepts of the present invention; and the prior art had much motivation for the present invention.

That is, it is emphasized that the prior art had several particulars of prior art and motivation which individually and accumulatively show the non-obviousness of this combination invention as to its various features:

Tubes, tubing, and various piping installations are devices which are of ancient use and knowledge, even tubing for use in many types of medical therapy, and specifically including tubing harnesses for respiration assistance and respiration monitoring; and such tubing and tubing fittings, including those of flexible material, have been used by an untold numbers of persons, the world over.

Further non-obviousness of the invention is shown by the fact that fittings for tubing have been made from material having flexibility, and by plastic molding procedures which have provided shoulders and other changes of diameter, etc.

With the reality of all these factors, the inventive non-obviousness of the present invention is quite manifest.

The prior art has had features of the present invention, and approaches to its concepts, but not in the combination by which the invention as a whole is advantageously achieved The background of prior art as just summarized seems more significant in showing the nonobviousness of the present concepts when also it is reminded that the prior art also had and used principles of insertability in diverse and innumerable assembly procedures.

Moreover, materials having considerable flexibility are of course quite well known, and known in even uses of medical equipment of various natures.

Molding and other manufacturing procedures are well known by which all components of the present invention could be made.

Joined and/or joinable fittings for hoses and tubing are also known in the prior art.

The prior art has tried a variety of types of respiratory harnesses, and tubing for each of oxygen supply and for monitoring the breathing cycles. And the existence of such articles embodying such various features is not only conceded, it is emphasized; for as to the novelty here of the combination, of the invention as considered as a whole, a contrast to the prior art helps show both the great variety and the dissatisfaction of the various prior art attemps of improvement, and the advantages and the inventive significance of the present concepts. Thus, as shown herein as a contrast to all the prior art, the inventive significance of the present concepts as a combination is emphasized, and the nature of the concepts and their results can perhaps be easier understood.

Although varieties of prior art are conceded, and ample motivation is shown, and full capability in the prior art is conceded, no prior art shows or suggests details of the overall combinations of the present invention, as is the proper and accepted way of considering the inventiveness nature of the concepts.

That is, although the prior art shows an approach to the overall invention, of tubing for oxygen-supply and for monitoring, and the prior art has shown various natures of tubing and fittings, including flexibility, etc., it is significant that none of the prior art shows the novel and advantageous combination, which provides the merits of this invention, even though certain details are shown separately from this accomplishment.

Accordingly, the various concepts and components are conceded and emphasized to have been widely known in the prior art as to various devices; nevertheless, the prior art not having had the particular combination of concepts and details as here presented and shown in novel combination different from the prior art and its suggestions, even only a fair amount of realistic humility, to avoid consideration of this invention improperly by hindsight, requires the concepts and achievements here to be realistically viewed as a novel combinations, inventive in nature. And especially is this a realistic consideration when viewed from the position of a person of ordinary skill in this art at the time of this invention, and without trying to reconstruct this invention from the prior art without use of hindsight toward particulars not suggested by the prior art of all relevant fields.

BRIEF DESCRIPTION OF THE DRAWINGS

The above description of the novel and advantageous invention is of somewhat introductory and generalized form. More particular details, concepts, and features are set forth in the following and more detailed description of an illustrative embodiment, reference being had to the accompanying somewhat schematic drawings, in which:

FIG. 1 is an overall view of a cannula harness having a dual lumen cannula pair according to the present invention;

FIG. 2 is an enlarged cross-sectional view of the hoses or tubing used in the device of FIG. 1, shown generally as taken by Section-line 2—2 of FIG. 1;

DETAILED DESCRIPTION OF THE ILLUSTRATIVE EMBODIMENT

Figure 3:
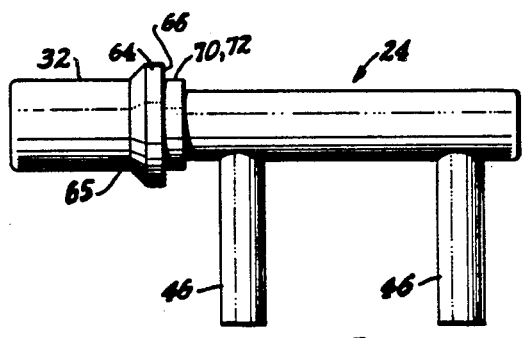
FIG. 3 and 4 are exterior views of an inner hose fitting and an outer hose fitting, respectively, which in their assembly provide an overall body member as shown in FIG. 5.
Figure 4:
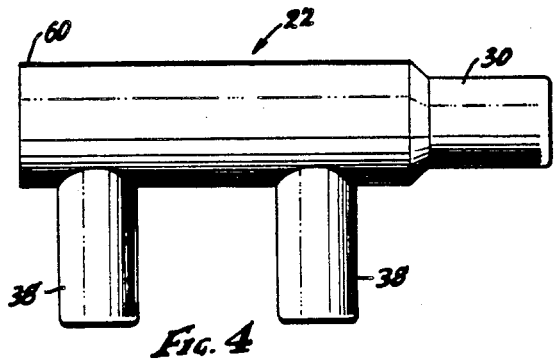

As shown in the drawings, the invention provides cannula apparatus 10 for providing modified respiration to a patient, and the monitoring of the respiration of the patient.

More particularly, such cannula apparatus 10 in a typical use is for use with associated supply equipment, such as oxygen-supply equipment (shown diagrammatically at 12) for the providing of a supply of associated gas such as oxygen for the providing of modified respiration; and the cannula apparatus 10 as shown is typically used also, and concurrently, with associated control equipment 14 for controlling the associated gas supply equipment 12, corresponding to the monitoring function, and thereby controlling the delivery of the associated gas to the cannula apparatus 10. (The control equipment 14 is also shown merely diagrammatically.)

In the typical use of an oxygen or oxygen/air supply and a breathing-monitor function, as in FIG. 1, the associated equipment 12 is shown as provided with a gas delivery hose 16, and the monitor equipment 14 is shown provided with a monitoring hose 18, schematically shown as respectively connected to and communicating with the gas supply 12 and the monitored control equipment 14.

The hoses or tubing 16/18 are desirably of a "peel-apart" type, and typically as shown will be of identical size, both as to inside diameter and outside diameter.

Turning now to the invention particulars, the cannula apparatus 10, not considering the hoses 16/18, comprises an assembly 20 of a pair of generally cylindrical body members here shown as a first (or "outer" for reasons apparent below) body member 22 and a second (or "inner" for reasons apparent below) body member 24; and it is by the assembly 20 of these members 22/24 that the pair of dual lumen cannulae are provided.

Each of the first body member 22 and the second body member 24 has a generally hollow primary bore, respectively 26 and 28, and are respectively provided with an inlet respectively 30 and 32 communicating the respective primary bore 26/28 with one of the respective gas delivery hose 16 and monitoring hose 18.

Figure 5:
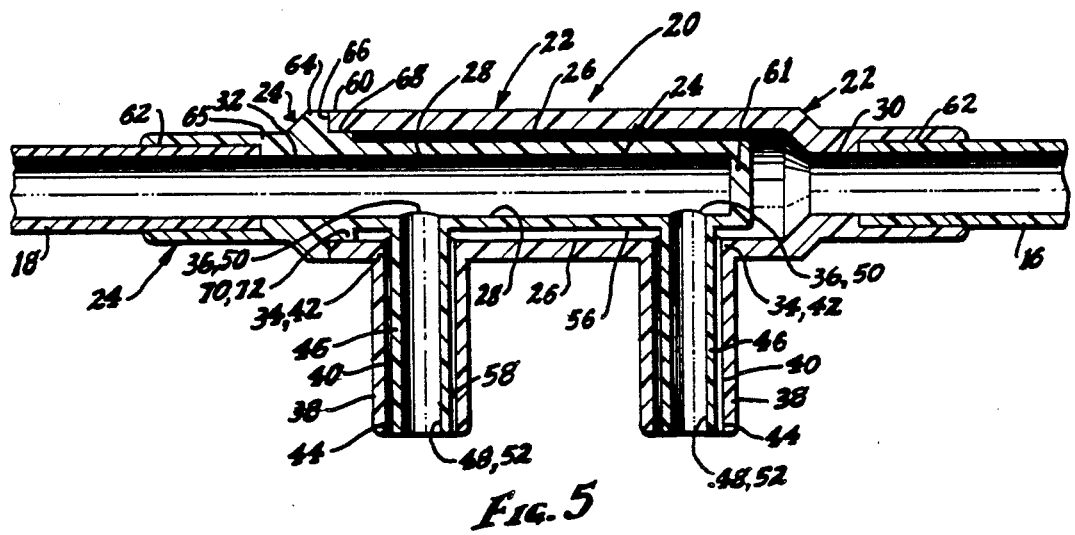
FIG. 5, in enlarged scale, is an axial cross-sectional view of the assembly of the fittings of FIG. 3 and 4, each of the two cannulae providing a generally concentric pair of bores respectively communicating with one of the hoses of FIG. 1, with and fragments of those hoses shown as connected respectively to those fittings.

Each of the primary bores 26/28 also is shown as having a pair of outlets, respectively 34 and 36, each pair of those outlets 34 and 36 being correspondingly spaced, thus registering when the fittings 22/24 are assembled, as shown in FIG. 5.

The first or outer body member 22 is provided with two cannula nipples 38, each having a generally hollow secondary lumen or bore 40; and each of the secondary bores 40 of the cannula nipples 38 of the first or outer body member 22 has an inlet 42 and an outlet 44; and the inlet 42 of the secondary bores 40 of the two cannula nipples 38 of the first body member 22 communicates directly with a respective one of the outlets 34 of the primary bore 26 of the first body member 22.

The second or inner body member 24 is quite similar to the first or outer body member 22, as now particularized and as apparent from the drawings.

That is, the second or inner body member 24 is provided with two cannula nipples 46 each having a generally hollow secondary lumen or bore 48, each of the secondary bores 48 of the cannula nipples 46 of the second or inner body member 24 having an inlet 50 and an outlet 52.

Similarly to those of the first body member 22, the inlet 50 of the secondary bores 48 of the two cannula nipples 46 of the second or inner body member 24 communicates directly with a respective one of the outlets 36 of the primary bore 28 of the second or inner body member 24.

As also shown best in FIG. 5, the pair of cannula nipples 38 of the first or outer body member 22 and the pair of cannula nipples 46 of the second or inner body member 24 are correspondingly spaced; and the portion of the second body member 24 having the two outlets 36 of its primary bore 28 is located within the primary bore 26 of the first or outer body member 22, and, when assembled as in FIG. 5, the cannula nipples 46 of the second or inner body member 24 are located within the secondary bore 40 of the respective cannula nipples 38 of the first or outer body member 22.

The spacing of the sets of cannulae 38/46 is quite short, i.e., just enough to straddle the cartilage between a person's nostrils for the insertion of the cannulae 38 containing the cannulae 46; and the transverse length of the cannulae 38/46 as shown in FIG. 5 is such that when the fittings 22/24 are assembled they end in a common plane.

Assembly to the condition of FIG. 5 is achieved by providing that the cannula nipples of the second or inner body member 24 are provided to be sufficiently resiliently flexible that the second body member 24 may be assembled into the primary bore 26 of the first body member 22, and the cannula nipples 46 of the second body member 24 assembled into the secondary bore 40 of the respective cannula nipples 38 of the first body member 22, by relatively pushing the second body member 24, axially of the primary bore 26 of the first body member 22, into the primary bore 26 of the first body member 22.

In such assembly, the flexibility accommodates the flexing and bending of the cannulae 46 of the second body member 24 during the insertion; and the resilience causes them to spring into the secondary bores 40 of the cannulae 38 of the first body member, as shown in FIG. 5 as assembled.

The accommodation of interchangeability is now explained.

That is, the cross-sectional area of the primary bore 28 of the second body member 24 is operatively the same as the difference between the cross-sectional area of the primary bore 26 of the first body member 22 and the cross-sectional area of the outer portion 56 of the second body member 24. That operative sameness of cross-sectional areas provides that it is a matter of substantial indifference which of the first or outer body member's inlet 30, or second or inner body member's inlet 32, is operatively connected to the gas delivery hose 16 or the monitoring hose 18.

Similarly providing that interchangeability is the area consideration of the sets of assembled cannulae 38/46 and 38/46.

More particularly, that is, as to each pair of cannula nipples 38 of the first body member 22 and of nipples 46 of the second body member 24, the cross-sectional area of the secondary bore 48 of each cannula nipple 46 of the second or inner body member 24 is operatively the same as the difference between the cross-sectional area of the secondary bore 40 of the respective cannula nipple 38 of the first or outer body member 22 and the cross-sectional area of the outer portion 58 of the cannula nipple 46 of the second body member 24.

That relationship, of an operative sameness of cross-sectional areas, also provides that it is a matter of substantial indifference which of the first body member's inlet 30 or second body member's inlet 32 is operatively connected to the gas delivery hose 16 or the monitoring hose 18.

(The word "operative", as used with respect to the cross-sectional areas mentioned, considers not only reasonable dimensional tolerances but the factor that fluid flow and/or restriction is a function of wall area as well as open area.)

The cannula apparatus 10 thus provides a cannula nipple 38/46 with a dual outlet 44/52 for each of a person's nostrils, in proximity to one another, for both delivering gas to each of the person's nostrils, and monitoring the respiration of the person by monitoring the respiration as to each of the person's nostrils. And, interchangeability is also achieved, as described herein.

OTHER DETAILS, AND SUMMARY AS TO USE

The operativity should be manifest by the drawings and the above description. That is, the flexibility of the inner fitting or second body member 24, and particularly of its transverse cannula nipples 46, permits it to be pushed axially (rightwardly, FIG. 5) into the downstream axial outlet 60 of the outer fitting or first body member 22; and cannula nipples 46 of the inner body member 24 then spring into the respective bores or lumens 40 of the transverse cannula nipples 38 of the outer fitting 22 as per FIG. 5. (The downstream end of the bore 28 of body member 24 is shown closed, at 61.)

Convenience is further achieved by operative equality of flow areas as specified, making it indifferent as to which of the tubing sections 16 and 18 are connected to the oxygen-supply equipment or breathing monitoring equipment, or, similarly, to which of the tubing sections 16 and 18 it is that each of the inner fitting 22 or outer fitting 24 body members are connected.

Also, accommodating an interchange of fittings 22 and 24, and hoses 16 and 18, it will be noted that the upstream cylindrical end portions 30 and 32 of both fittings 22 and 24 are of the same inner diameter, they both being shown as recessed or counterbored (62) to receive the hoses 16/18, all shown the same diameter as the bore 28 of body member 24.

The outer shoulder 64 on the inner fitting 24, adjacent its upstream end 65, provides a stop 66 against which the downstream end 60 of the outer fitting 22 is pushed, assuring a length of closure engagement of the inner cylindrical wall 68 of the downstream end 60 of the outer fitting 24 against the outer surface 70 of the raised or enlarged diameter portion 72 of the inner fitting 24 just downstream of that inner fitting shoulder 64 adjacent its upstream end 65.

If two gases "A" and "B" are to be supplied instead of one being a monitoring line, for brevity it is mentioned merely that the same embodiment is illustrative, except that line 18 would be another gas line, with equipment 14 being that of that gas supply line; but the description including interchangeability of fitting 22/24 and/or tubing lines 16/18 applies as above described.

CONCLUSION

It is thus seen that a cannula harness or the like, provided and used according to the inventive concepts herein set forth, provides novel concepts of a desirable and advantageous device, yielding the advantages of an overall combination of respiration equipment providing a pair of lumens for each of two cannulae, interchangeably useful for providing a gas and a monitor, or two gases, particularly for respiration-assisted therapy, which, in overall combination, is conceptually different from the prior art even though objects embodying certain of the mechanical details as a basic capability have of course been known for years; yet significantly this particular combination, even considered as including or building on prior art concepts has not been suggested by the prior art, this achievement being a substantial and advantageous departure from prior art, even though the prior art shows attempts at improvement and variations as to oxygen therapy and other respiration-assisted therapy for many years. And particularly is the overall difference from the prior art significant when the non-obviousness is viewed by a consideration of the subject matter as a whole, as integrally incorporating a combination of features as different from the prior art, in contrast to merely those details of novelty themselves, and further in view of the prior art teaching away from the particular and inter-related concepts and features of the present invention.

In summary as to the nature of these advantageous concepts, their inventiveness is shown by novel features of concept and construction shown here, in novel and advantageous combination, not only being different from all the prior art known, but because the achievement is not what is or has been suggested to those of ordinary skill in the art, especially realistically considering this as comprising components which individually are similar in nature to what is well known to makers and users of respiration-assisting tubing for many years. No prior art has suggested the modifications of any prior art to achieve the novel concepts here achieved, with the various features providing their own functions in the overall combination.

Accordingly, it will thus be seen from the foregoing description of the invention according to this illustrative embodiment, considered with the accompanying drawings, that the present invention provides new and useful concepts of a novel and advantageous respiration-assisting device having and yielding desired advantages and characteristics in formation and use, and accomplishing the intended objects, including those hereinbefore pointed out and others which are inherent in the invention.

Modifications and variations may be effected without departing from the scope of the novel concepts of the invention; accordingly, the invention is not limited to the specific embodiment, or form or arrangement of parts herein described or shown.

I claim:

1. Cannula apparatus providing for modified respiration and the monitoring thereof as to a human patient,
    for use with (a) associated supply equipment for the providing of a supply of associated gas for providing the modified respiration, and with (b) associated control equipment for controlling the associated supply equipment and thereby controlling the delivery of the associated gas to the cannula apparatus,
    the associated equipment being provided with a gas delivery hose and a monitoring hose, respectively for communication with the gas supply and the control equipment;
    the cannula apparatus comprising:
    a first body member and a second body member;
    each of the first body member and the second body member having a generally hollow primary bore, and each of the first body member and second body member being provided with an inlet communicating the respective primary bore with one of the respective gas delivery hose and monitoring hose;
    and the primary bore of each of the first body member and second body member also having a pair of outlets;
    the first body member being provided with two cannula nipples, each of said nipples having a generally hollow secondary bore, and the said secondary bore of each of the cannula nipples of the first body member having an inlet an an outlet,
    the inlet of the said secondary bore of each of the two cannula nipples of the first body member communicating directly with a respective one of the said two outlets of the primary bore of the first body member;
    the second body member being provided with two cannula nipples, each of said nipples having a generally hollow secondary bore, and the said secondary bore of each of the cannula nipples of the second body member having an inlet and an outlet,
    the inlet of the said secondary bore of each of the two cannula nipples of the second body member communicating directly with a respective one of the said two outlets of the primary bore of the second body member;
    the pair of cannula nipples of the first body member and the pair of cannula nipples of the second body member being correspondingly spaced, and the portion of the second body member having the two outlets of its primary bore being located within the primary bore of the first body member, and the cannula nipples of the second body member being located within the secondary bore of the respective cannula nipples of the first body member;
    the cannula apparatus providing a cannula nipple outlet for each of a person's nostrils in proximity to one another for both delivering gas to each of the person's nostrils, and monitoring the respiration of the person by monitoring the respiration as to each of the person's nostrials.

2. The cannula apparatus as set forth in claim 1, in a combination in which the cannula nipples of the second body member are provided to be sufficiently resiliently flexible that the second body member may be assembled into the primary bore of the first body member, and the cannula nipples of the second body member into the secondary bore of the respective cannula nipples of the first body member, by relatively pushing the second body member into the primary bore of the first body member.

3. The cannula apparatus as set forth in claim 1, in a combination in which the cross-sectional area of the primary bore of the second body member is operatively the same as the difference between the cross-sectional area of the primary bore of the first body member and the cross-sectional area of the outer portion of the second body member, the operative sameness of cross-sectional areas providing that it is a matter of substantial indifference which of the first body member's inlet or second body member's inlet is operatively connected to the gas delivery hose or the monitoring hose.

4. The cannula apparatus as set forth in claim 1, in a combination in which, as to each pair of cannula nipples of the first body member and second body member, the cross-sectional area of the secondary bore of each cannula nipple of the second body member is operatively the same as the difference between the cross-sectional area of the secondary bore of the respective cannula nipple of the first body member and the cross-sectional area of the outer portion of the cannula nipple of the second body member;

the operative sameness of cross-sectional areas providing that it is a matter of substantial indifference which of the first body member's inlet or second body member's inlet is operatively connected to the gas delivery hose or the monitoring hose.

5. The cannula apparatus as set forth in claim 2, in a combination in which the cross-sectional area of the primary bore of the second body member is operatively the same as the difference between the cross-sectional area of the primary bore of the first body member and the cross-sectional area of the outer portion of the second body member, the operative sameness of cross-sectional areas providing that it is a matter of substantial indifference which of the first body member's inlet or second body member's inlet is operatively connected to the gas delivery hose or the monitoring hose.

6. The cannula apparatus as set forth in claim 2, in a combination in which, as to each pair of cannula nipples of the first body member and second body member, the cross-sectional area of the secondary bore of each cannula nipple of the second body member is operatively the same as the difference between the cross-sectional area of the secondary bore of the respective cannula nipple of the first body member and the cross-sectional area of the outer portion of the cannula nipple of the second body member;

the operative sameness of cross-sectional areas providing that it is a matter of substantial indifference which of the first body member's inlet or second body member's inlet is operatively connected to the gas delivery hose or the monitoring hose.

7. The cannula apparatus as set forth in claim 3, in a combination in which, as to each pair of cannula nipples of the first body member and second body member, the cross-sectional area of the secondary bore of each cannula nipple of the second body member is operatively the same as the difference between the respective cross-sectional area of the secondary bore of the cannula nipple of the first body member and the cross-sectional area of the outer portion of the cannula nipple of the second body member;

the operative sameness of cross-sectional areas providing that it is a matter of substantial indifference which of the first body member's inlet or second body member's inlet is operatively connected to the gas delivery hose or the monitoring hose.

8. Cannula apparatus providing for modified respiration involving gasses "A" and "B" as to a human patient, for use with (a) associated supply equipment for providing for the patient a supply of associated gas "A", and with (b) associated supply equipment for providing for the patient a supply of associated gas "B", the associated supply equipments being provided respectively with a gas "A" delivery hose and a gas "B" delivery hose, respectively for communication of the gas "A" supply and the gas "B" supply with the cannula apparatus;

the cannula apparatus comprising:

a first body member and a second body member;

each of the first body member and the second body member having a generally hollow primary bore, and each of the first body member and second body member being provided with an inlet communicating the respective primary bore with one of the respective gas "A" delivery hose and gas "B" delivery hose for receiving gas "A" and gas "B" respectively;

and the primary bore of each of the first body member and second body member also having a pair of outlets;

the first body member being provided with two cannula nipples, each of said nipples having a generally hollow secondary bore, and the said secondary bore of each of the cannula nipples of the first body member having an inlet and an outlet, the inlet of the said secondary bore of each of the two cannula nipples of the first body member communicating directly with a respective one of the said two outlets of the primary bore of the first body member;

the second body member being provided with two cannula nipples, each of said nipples having a generally hollow secondary bore, and the said secondary bore of each of the cannula nipples of the second body member having an inlet and an outlet, the inlet of the said secondary bore of each of the two cannula nipples of the second body member communicating directly with a respective one of the said two outlets of the primary bore of the second body member;

the pair of cannula nipples of the first body member and the pair of cannula nipples of the second body member being correspondingly spaced, and the portion of the second body member having the two outlets of its primary bore being located within the primary bore of the first body member, and the cannula nipples of the second body member being located within the secondary bore of the respective cannula nipples of the first body member;

the cannula apparatus providing a cannula nipple outlet for each of a person's nostrils in proximity to one another for delivering both gas "A" and gas "B" to each of the person's nostrils.

9. The cannula apparatus as set forth in claim 8, in a combination in which the cannula nipples of the second body member are provided to be sufficiently resiliently flexible that the second body member may be assembled into the primary bore of the first body member, and the cannula nipples of the second body member into the secondary bore of the respective cannula nipples of the first body member, by relatively pushing the second body member into the primary bore of the first body member.

10. The cannula apparatus as set forth in claim 8, in a combination in which the cross-sectional area of the primary bore of the second body member is operatively the same as the difference between the cross-sectional area of the primary bore of the first body member and the cross-sectional area of the outer portion of the second body member, the operative sameness of cross-sectional areas providing that it is a matter of substantial indifference which of the first body member's inlet or second body member's inlet is operatively connected to the gas "A" delivery hose or the gas "B" delivery hose.

11. The cannula apparatus as set forth in claim 8, in a combination in which, as to each pair of cannula nipples of the first body member and second body member, the cross-sectional area of the secondary bore of each cannula nipple of the second body member is operatively the same as the difference between the cross-sectional area of the secondary bore of the respective cannula nipple of the first body member and the cross-sectional area of the outer portion of the cannula nipple of the second body member;

the operative sameness of cross-sectional areas providing that it is a matter of substantial indifference which of the first body member's inlet or second body member's inlet is operatively connected to the gas "A" delivery hose or the gas "B" delivery hose.

12. The cannula apparatus as set forth in claim 9, in a combination in which the cross-sectional area of the primary bore of the second body member is operatively the same as the difference between the cross-sectional area of the primary bore of the first body member and the cross-sectional area of the outer portion of the second body member, the operative sameness of cross-sectional areas providing that it is a matter of substantial indifference which of the first body member's inlet or second body member's inlet is operatively connected to the gas "A" delivery hose or the gas "B" delivery hose.

13. The cannula apparatus as set forth in claim 9, in a combination in which, as to each pair of cannula nipples of the first body member and second body member, the cross-sectional area of the secondary bore of each cannula nipple of the second body member is operatively the same as the difference between the cross-sectional area of the secondary bore of the respective cannula nipple of the first body member and the cross-sectional area of the outer portion of the cannula nipple of the second body member;

the operative sameness of cross-sectional areas providing that it is a matter of substantial indifference which of the first body member's inlet or second body member's inlet is operatively connected to the gas "A" delivery hose or the gas "B" delivery hose.

14. The cannula apparatus as set forth in claim 10, in a combination in which, as to each pair of cannula nipples of the first body member and second body member, the cross-sectional area of the secondary bore of each cannula nipple of the second body member is operatively the same as the difference between the cross-sectional area of the secondary bore of the respective cannula nipple of the first body member and the cross-sectional area of the outer portion of the cannula nipple of the second body member;

the operative sameness of cross-sectional areas providing that it is a matter of substantial indifference which of the first body member's inlet or second body member's inlet is operatively connected to the gas "A" delivery hose or the gas "B" delivery hose.

* * * * *

UNITED STATES PATENT AND TRADEMARK OFFICE
CERTIFICATE OF CORRECTION

PATENT NO. : 4,989,599

DATED : February 5, 1991

INVENTOR(S) : William Carter

It is certified that error appears in the above-identified patent and that said Letters Patent is hereby corrected as shown below:

Col. 1, line 2, Should have Roman numeral --I.-- before the word "FIELD".

line 39, Should have Roman numeral --II.-- before the word "SUMMARY".

Col. 2, lines 1-3 --Should show as a heading--.

Col. 3, lines 4-7 --Should show as a heading--.

Signed and Sealed this

Eighteenth Day of May, 1993

Attest:

MICHAEL K. KIRK

Attesting Officer

Acting Commissioner of Patents and Trademarks